United States Patent [19]

Ciaglia et al.

[11] Patent Number: 5,279,567
[45] Date of Patent: Jan. 18, 1994

[54] TROCAR AND TUBE WITH PRESSURE SIGNAL

[75] Inventors: Pasqule Ciaglia, Utica; John S. Gentelia, Madison, both of N.Y.

[73] Assignee: Conmed Corporation, Utica, N.Y.

[21] Appl. No.: 907,801

[22] Filed: Jul. 2, 1992

[51] Int. Cl.$^5$ ............................................. A61M 5/00
[52] U.S. Cl. ................................ 604/117; 604/164; 128/748
[58] Field of Search ............... 604/117, 131, 158, 164, 604/264, 267, 272, 118; 606/80, 167, 170, 180, 185; 128/748

[56] References Cited

U.S. PATENT DOCUMENTS

| | | | |
|---|---|---|---|
| 2,922,426 | 1/1960 | Cheng | 604/272 |
| 4,191,191 | 3/1980 | Auburn | 604/188 |
| 4,810,244 | 3/1989 | Allen | 604/164 |
| 5,009,643 | 4/1991 | Reich et al. | 604/167 |
| 5,147,376 | 7/1992 | Pianetti | 604/170 |
| 5,188,594 | 2/1993 | Zilberstein | 128/748 |

FOREIGN PATENT DOCUMENTS

| | | | |
|---|---|---|---|
| 1541237 | 7/1969 | Fed. Rep. of Germany | 604/264 |
| 1521465 | 11/1989 | U.S.S.R. | 604/264 |

*Primary Examiner*—John D. Yasko
*Assistant Examiner*—Anthony Gutowski
*Attorney, Agent, or Firm*—Larson & Taylor

[57] ABSTRACT

An apparatus for inserting a thoracotomy tube in a patient without damaging adjacent lung tissues is provided. The thoracotomy tube is adapted to receive a trocar having screw threads on the distal end thereof. The proximal end of the trocar has a handle thereon to rotate the trocar so that the screw threaded distal end forms an incision within the skin of the patient and the tip end of the screw thread passes into the pleural cavity. The distal end of the thoracotomy tube is provided with screw threads on the outer surface thereof to form a continuation of the screw threads of the trocar. The distal tip or end of the trocar terminates in a short flexible tube. A hollow needle extends through a central passageway in the trocar and through the flexible tip on the trocar. The opposite end of the hollow needle is provided with a pressure chamber which is in fluid communication with the passageway in the needle. In use, the trocar and thoracotomy tube are screwed into the body tissues of the patient and when the distal end of the needle enters the pleural cavity within the body, liquid within the pressure chamber passes through the hollow needle and into the pleural cavity. The release of the fluid from the pressure chamber is an indicator to the surgeon that the end portion of the needle has entered the pleural space. The trocar and thoracotomy tube are then screwed in as the needle is withdrawn from the flexible tip on the distal end of the trocar so as to prevent damage to any body tissues.

2 Claims, 1 Drawing Sheet

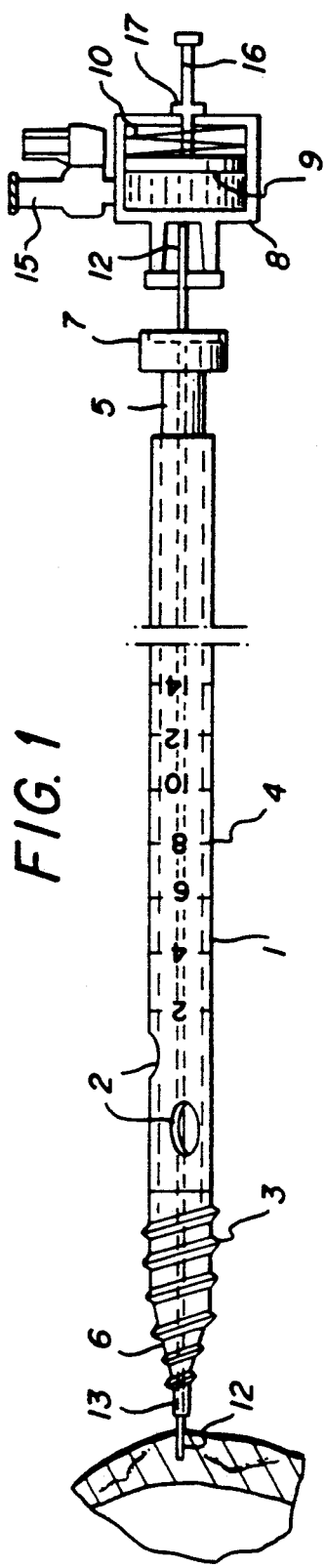
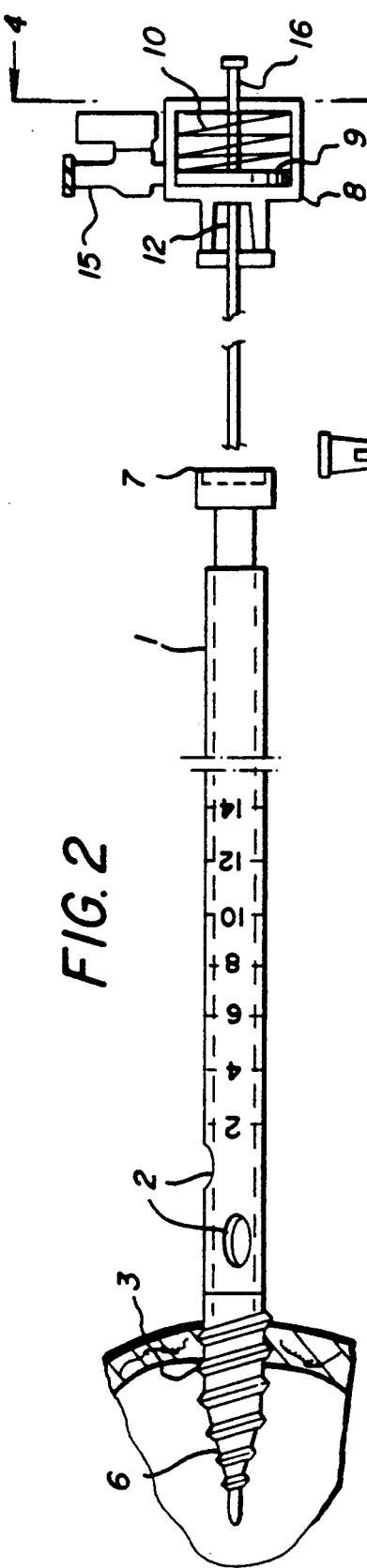
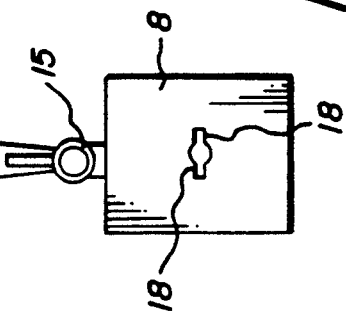
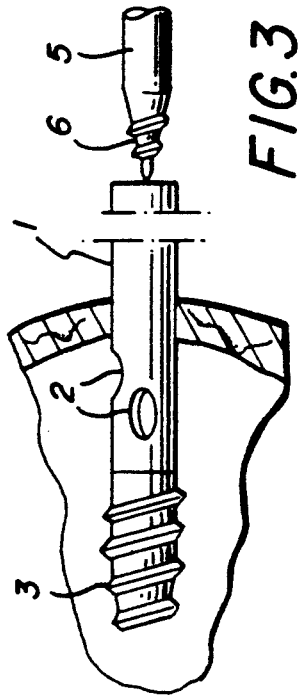

TROCAR AND TUBE WITH PRESSURE SIGNAL

BACKGROUND OF THE INVENTION

The present invention relates generally to a method and apparatus for inserting a tube within a body cavity and more specifically to a method and apparatus for inserting a thoracotomy tube within the pleural cavity of a patient.

Whenever an invasion of the chest cavity occurs, such as by a stab wound or heart operation or the like, it is necessary to provide a thoracotomy tube which extends from the pleural cavity to a pleural drainage device. The pleural drainage device serves to remove fluid collected within the pleural cavity and to maintain the proper degree of negativity within the pleural cavity so as to provide proper functioning of the lungs. Such pleural drainage devices are well known in the art and shown, for example, in U.S. Pat. Nos. 363,626 and 4,018,224.

Normally, the thoracotomy tubes are inserted between the ribs and frequently when the incisions are made to insert the thoracotomy tubes, lung tissue is damaged due to too deep penetration into the pleural cavity by the surgical knife. It is therefore important to limit the dept of the incision within the pleural cavity. The Baran U.S. Pat. No. 2,630,803 describes a method and apparatus for limiting the depth of the incision within the pleural cavity. Other prior art devices are shown for locating catheters and the like within the various body cavities. The Groshong U.S. Pat. No. 4,529,399, the Zorraquin U.S. Pat. No. 1,527,291, Silverman U.S. Pat. No. 3,433,214, Reif U.S. Pat. No. 3,508,545, Cimber U.S. Pat. No. 3,659,610 and Crag U.S. Pat. No. 4,772,264 are all examples of various devices for insertion of catheters or aspiration needles within body cavities. However, none of the foregoing devices meet the need of providing a simple structure which can quickly and efficiently provide an incision into the pleural cavity of a patient and locate a thoracotomy tube properly within the pleural cavity to give the patient prompt relief from a collapsing lung.

According to the present invention, there is provided a thoracotomy tube and trocar combination which enables a physician to locate a thoracotomy tube in the pleural cavity of a patient quickly and accurately without danger to lung tissues. The trocar has screw threads on the distal end thereof and is provided with an enlarged area at the proximal end to form a handle. The thoracotomy tube slidably receives the trocar and has a length such that the screw threaded distal end of the trocar extends approximately 2 centimeters beyond the distal end of the thoracotomy tube. In use, the trocar and thoracotomy tube are screwed into the body tissues of the patient and when the distal end of the needle enters the pleural cavity within the body, liquid within the pressure chamber passes through the hollow needle and into the pleural cavity. The release of the fluid from the pressure chamber is an indicator to the surgeon that the end portion of the needle has entered the pleural cavity. The trocar and thoracotomy tube are then screwed in as the needle is withdrawn from the flexible tip on the distal end of the trocar so as to prevent damage to any body tissues. The distal end of the thoracotomy tube has screw threads thereon so that after the initial incision is formed by the trocar, the thoracotomy tube may be screwed into the pleural cavity while the hollow needle is withdrawn. Thus, the thoracotomy tube may be quickly and accurately located within the pleural cavity without damage to lung tissues.

An object of the present invention is to provide a method and apparatus for accurately and quickly locating a thoracotomy tube within the pleural cavity of a patient.

Another object of the present invention is to provide a trocar having screw threads for forming an incision into the pleural cavity of a patient without damage to lung tissue.

Still another object of the present invention is to provide a trocar with screw threads thereon and a thoracotomy tube with continuing screw threads thereon to permit the trocar to form an incision and to provide a means for quickly locating the thoracotomy tube within the pleural cavity. Other objects and many of the attendant advantages of the present invention will be appreciated upon consideration of the following detailed description in connection with the accompanying drawings wherein:

BRIEF DESCRIPTION OF THE DRAWINGS

FIG. 1 shows a thoracotomy tube and trocar in position on the skin of a patient before the incision is to be made, FIG. 2 shows the trocar after the incision has been made, and hollow needle withdrawn, FIG. 3 shows the thoracotomy tube within the pleural cavity and the trocar withdrawn and, FIG. 4 is a top plan view along the lines 4—4 of FIG. 2.

DETAILED DESCRIPTION OF THE DRAWINGS

There is shown at 1 in FIG. 1 a thoracotomy tube which is formed of plastic and is relatively flexible. The thoracotomy tube is provided with openings 2 around the periphery of the tube at the distal end thereof. The thoracotomy tube also is provided with screw threads 3 which extend from the distal end around the end portion of the tube extending approximately 1 centimeter from the distal end of the thoracotomy tube. The thoracotomy tube further has markings along the length thereof as shown at 4 to indicate the penetration of the end of the thoracotomy tube within the pleural cavity. A radiopaque stripe (not shown) extending along the length of the thoracotomy tube also provides an indication of the extent of penetration of the distal end of the thoracotomy tube within the pleural cavity.

The trocar 5 is slidably received within the thoracotomy tube 1 and has the distal end thereof formed with screw threads 6 extending from a point at the tip end of the trocar to approximately 2 centimeters along the length of the trocar. The proximal end of the trocar has a handle 7 thereon to rotate the trocar and thoracotomy tube as one.

A hollow needle 12 is slidably disposed within the trocar 2 and extends through the distal end of the trocar and through a soft plastic tube 13 on the end of the trocar 5. The opposite end of the needle 12 extends beyond the proximal end portion of the trocar 5 and has attached thereto a pressure chamber 8. A pressure chamber 8 is provided with a piston 9 and spring 10 with a passageway interconnecting the pressure chamber 8 with the passageway extending through the length of the needle 12. There is provided a stopcock and port 15 mounted on the chamber 8 for introducing saline solutions or other fluids into the chamber 8. There is provided a plunger 16 which is rotatably attached to the piston 9 and extends upwardly through the opening in the top wall of chamber 8. The plunger 16 is provided with a pair of wings 17 (FIG. 1) affixed thereto which are adapted to slide through slots 18 in the top wall of the chamber 8, FIG. 4. Thus, when the plunger 16 is drawn upwardly to compress spring 10 and the plunger rotated so that the wings 17 are not in alignment with the slots 18, the piston is retained in an inoperative position.

In use, the trocar and thoracotomy tube are positioned as shown in FIG. 1 with the distal end of the trocar 1 in abutment with the skin of the patient. The surgeon holds the thoracotomy tube 1 in position against the skin and rotates the plunger 16 of the fluid filled chamber 8 so that the wings 17 are in alignment with slots 18. The spring 10 urges the piston 9 downwardly towards the open upper end of the hollow needle 12. The fluid within the chamber 8 is forced through the hollow needle 12, but the fluid cannot pass through the distal end of the needle 12 as the distal end of the needle is blocked by body tissue. The thoracotomy tube 1 may then be rotated so that the screw threads 3 are screwed through the incision into the pleural cavity. As soon as the end of the trocar 5 passes through the skin tissue and into the pleural cavity, the pressurized fluid within the hollow needle is released and passes into the pleural cavity. The release of fluid from the chamber 8 notifies the doctor that the trocar is within the pleural cavity. The trocar 5 may then be withdrawn through the thoracotomy tube. FIG. 3 shows the thoracotomy tube 1 in position within the pleural cavity with the trocar withdrawn.

The thoracotomy tube may be adjusted within the pleural cavity to any desired point since there is no danger of damage to lung tissues by the soft end of the thoracotomy tube. The markings 4 on the thoracotomy tube provide a means for determining the depth of the distal end of the thoracotomy tube within the body cavity. The radiopaque strips also provides a means for precisely locating the end of the thoracotomy tube. The openings 2 in the side wall of the thoracotomy tube provide a passageway for fluids within the pleural cavity to be withdrawn by suction applied through the pleural drainage device. The relationship of the length of the thoracotomy tube and the trocar prevent the possibility of damage to the patient's lungs by reason of insertion of the trocar too deeply within the pleural cavity. Thus, the presently disclosed invention provides a means for quickly and safely inserting a thoracotomy tube within a patient's pleural cavity.

Obviously many modifications and variations of the present invention are possible in light of the foregoing teachings.

What is claimed as new and is desired to be secured by Letters Patent is:

1. A device for inserting a tube in a body cavity of a patient comprising, in combination, a flexible tube having proximal and distal ends, a trocar slidably fitting within the tube, said trocar having proximal and distal ends, screw threads on the distal end of the trocar, said distal end of the trocar extending beyond the distal end of the tube whereby the trocar may form an incision into the skin and body tissues and into a body cavity of a patient and further including a lumen extending through the distal end of the trocar and signal means operatively connected to said lumen to indicate pressure variations within the lumen whereby the location of the distal end of the trocar within the body cavity may be determined so that the tube may be inserted into the body cavity as the trocar is removed.

2. A device according to claim 1, wherein said signal means comprises a fluid filled pressure chamber disposed adjacent the proximal end of the trocar and in fluid communication with the lumen and means for releasing the fluid within the pressure chamber when the distal end of the hollow needle passes into the body cavity.

* * * * *